United States Patent [19]

Markle et al.

[11] Patent Number: 4,943,460

[45] Date of Patent: Jul. 24, 1990

[54] PROCESS FOR COATING POLYMER SURFACES AND COATED PRODUCTS PRODUCED USING SUCH PROCESS

[75] Inventors: Richard A. Markle; Phyllis L. Brusky, both of Columbus; John H. Baker, Strasburg, all of Ohio

[73] Assignee: Snyder Laboratories, Inc., Dover, Ohio

[21] Appl. No.: 308,679

[22] Filed: Feb. 13, 1989

Related U.S. Application Data

[63] Continuation-in-part of Ser. No. 157,856, Feb. 19, 1988, abandoned.

[51] Int. Cl.$^5$ .............................................. B29D 22/00
[52] U.S. Cl. .................................. 428/36.9; 428/353; 428/451; 428/522; 523/112; 524/267; 524/266; 525/102; 604/265
[58] Field of Search ............. 428/353, 451, 522, 36.9; 604/265; 523/112; 525/102; 524/267, 266

[56] References Cited

U.S. PATENT DOCUMENTS

| | | | |
|---|---|---|---|
| 4,119,094 | 10/1978 | Micklus et al. | 428/424.6 |
| 4,439,479 | 3/1984 | Kanai et al. | 428/480 |
| 4,666,437 | 5/1987 | Lambert et al. | 428/423.7 |

*Primary Examiner*—Edith Buffalow
*Attorney, Agent, or Firm*—Richard H. Brink

[57] ABSTRACT

Processes for treating polymeric surfaces to produce smooth, durable, slippery coatings which are able to withstand the rigors of sterilization and, long term exposure to human blood and other bodily fluids without substantial loss of their slipperiness.

16 Claims, No Drawings

PROCESS FOR COATING POLYMER SURFACES AND COATED PRODUCTS PRODUCED USING SUCH PROCESS

The present application is a continuation in part of Ser. No. 157,856 filed Feb. 19, 1988 now abandoned.

FIELD OF THE INVENTION

This invention relates to the field of coatings for polymer surfaces and particularly to processes for treating polymeric surfaces to produce smooth, durable, slippery coatings which are able to withstand the rigors of sterilization and long term exposure to human blood and other body fluids without substantial loss of their slipperiness. More particularly this invention relates to a process for coating surgical devices made of various polymeric materials to provide a superior, smooth, durable slippery coating thereon.

BACKGROUND OF THE INVENTION

The use of devices made from various polymeric materials, including silicone rubber and polyvinyl chloride (PVC) and the like, has achieved an important place in carrying out numerous surgical procedures. An important class of such devices consists of various wound drainage devices, surgical inserts and surgical tubing all of which are important in the removal of blood and other fluids from a surgical or wound site.

Generally speaking in the course of such procedures a tubular device made of some inert, usually polymeric, material must be inserted and positioned through body tissue and must allow unrestricted flow of blood through the device for up to several days. The presently available devices, especially those made of silicone, have undesirably high resistance to movement through tissue. A greater problem is an undesirably high level of blood clot formation inside drainage tubes, especially those made from silicone and PVC. Most serious of all, the clots which form, especially in silicone, are difficult to remove. These undesirable characteristics primarily derive from the fact that silicone rubber tubing has a very hydrophobic surface which is very poorly wetted by aqueous media. Devices made from PVC, although better performing than silicone, also have poorly wetted, nonslippery surfaces.

Thus it has been deemed desirable to develop a process which would allow one to coat the surfaces of devices made from various polymeric materials, such as for example silicone and PVC, to improve the wettability and slipperiness of such devices, particularly under conditions encountered when such devices are employed in wound drainage applications.

Amongst the prior art of which the applicants are aware dealing with the problem of coating various polymeric materials in contact with human body fluids are the following:

U.S. Pat. No. 4,100,309 discloses a multistep method of applying a hydrophilic coating on a substrate.
U.S. Pat. No. 4,119,094 is related to U.S. Pat. No. 4,100,309 and claims articles coated in accordance with the process set out therein.
U.S. Pat. No. 3,925,178 discloses a process for treating a plastic contact lens to make the lens surface hydrophilic without changing the optical characteristics of the lens.
U.S. Pat. No. 4,312,575 also discloses contact lenses having an ultrathin, clear, lipid-permeable hydrophilic barrier coating which is formed by an electrical glow discharge process.
U.S. Pat. No. 4,589,873 teaches the coating of vinyl tubing with a DMF solution of PVP.

None of the foregoing references teaches the process or the products produced thereby which are the subject of the present invention.

SUMMARY OF THE INVENTION

The present invention is directed to a process for treating polymeric surfaces to produce smooth durable slippery coatings which are particularly suited for use as wound drainage or other surgical devices. Products made from such coated polymeric materials are also taught herein.

DESCRIPTION OF THE INVENTION

It has been found that producing a hydrogel surface on a silicone, PVC, latex, polyester, polyurethane or thermoplastic elastomer surface, that is, one which is wettable and slippery in water, will substantially improve the performance of wound drainage devices constructed from silicone rubber and PVC. For example, the frictional forces produced by the surfaces of such devices by inserting or removing them through tissue will be greatly reduced. More importantly the tendency for the blood to clot has been shown to be lessened and the ease of clot removal is greatly enhanced by such a surface. Also, it is generally recognized that a fluorinated surface (i.e. Teflon or Teflon-like) is much less prone to blood clot formation (i.e. is less thrombogenic) than a silicone rubber or PVC surface, probably because it has a lower energy surface, and a lower coefficient of friction. Hence, low energy fluorinated surfaces are also expected to produce surfaces with lesser blood clotting tendencies and less adherence of blood clots if they do form.

The object of the present invention is a process or treatment which will provide improved surface properties to wound or surgical drainage devices made from various polymeric materials, including silicone and PVC. The improved surface properties to be achieved will consist of either a more wettable, slippery surface, or a lower energy, less thrombogenic surface. These characteristics are to be provided, respectively, via physically or chemically anchored hydrogel polymer coatings, or by a fluorinated or polyfluorocarbon coated silicone rubber and PVC surface. The modified polymeric surface must meet four conditions or criteria to be successful.

The criteria, or specifications, for an acceptably treated (coated) wound drainage device are the following:

1. The modified surface must retain this characteristic for a minimum of 100 hours when in contact with wound secretions.
2. The process and/or condition which produces such a surface must be applicable to the inside and outside diameters of round tubes and irregular cross-sectional shaped tubes. These round tubes and/or combinations of irregular shapes are known as closed wound drainage devices, usually used in combination with a suction device; such as Snyder Hemovac ™ or Surgivac ™.
3. The modified surface must be able to withstand an ethylene oxide sterilization process and not deteriorate, crack, have an adversely affected shelf-life, or impair the physical characteristics or properties of the polymeric substrate layer or surface.

4. The process and/or condition which produces such a surface must be safe (e.g., FDA approvable, pass USP XIX class VI), reasonable and feasible to scale-up in a continuous, semi-continuous or batch manufacturing mode.

It should be understood that there are significant differences for example between silicone rubber (cross-linked polydimethysiloxane) and flexible vinyl (PVC). The basic polymer structures are as follows:

However, the silicone as used is a filled (silica), crosslinked (i.e., three dimensional, insoluble network) rubber, while the PVC is a soluble thermoplastic containing a potentially solvent leachable plasticizer and no filler. The silicone is a relatively stable, low surface energy (highly nonwater-wettable) material while PVC has an intermediate surface energy and water wettability and is relatively susceptible to reaction due to the chlorine-carbon bonds (loss of HCL via heat or strong base, possible quaternization with amines). However, the silicone has some residual chemically reactive silane (SiH) and/or vinyl (SiCH=CH$_2$) groups. These were the groups used to cure (cross-link) the rubber. They are potentially usable for chemical attachment (grafting), if they are present in sufficient concentration, on or near the tubing surface. The silica filler in the silicone also possesses reactive surface silanol (SiOH) groups usable for grafting, again if a sufficient concentration of these groups is at or just below the rubber surface, to provide a useful degree of bonding.

A complication with PVC is the presence of the organic ester (e.g. dioctyl phthalate) plasticizer, which possibly can migrate (bloom) to the surface and interfere with surface reactions, and/or be leached out during solution or solvent treatment, perhaps resulting in a hardened, more brittle or crack-prone surface.

However, it must be remembered that vinyl tubing is not cross-linked and any organic liquid which is a solvent for PVC will dissolve or erode the tubing. This is in contrast to the silicone tubing, which is cross-linked and swells but cannot dissolve in a liquid which is a solvent for uncrosslinked silicone. Hence silicone rubber can be easily and conveniently impregnated with a number of potential coupling or grafting agents, using a range of solvents and soaking conditions, while solvent solutions for treating vinyl must be chosen and used with care.

Hence, although some coating or treating methods can be used on both silicone, PVC and other polymeric materials, the special requirements of the substrates' surfaces must be kept in mind and the procedures adapted to the surfaces as required; some possible treatment procedures will be unique to the particular surface utilized.

In carrying out the experimental work necessary to evaluate the process of the present invention, silicone rubber was swollen with an appropriate swelling solvent, such as methylene chloride or 1,1,1-trichloroethane, the rubber impregnated with the selected attachment or curing agent and the selected polymer coated from an appropriate organic solvent or water solution as appropriate. Variable drying/heat curing processes were used to obtain adherent coatings. It may be necessary to selectively post-treat the coated sample with the same, or possibly a different, crosslinking or curing agent to render the coating water insoluble, yet water swellable, to prevent dissolution or premature erosion of the coating.

PVC treatment was approached more cautiously due to the solubility of the substrate. The best solvent treatment medium was determined by comparing the effect of a series of solvents on PVC. Alcohols were found to be the best medium for treatment.

It is potentially beneficial to pretreat the polymeric surface to be coated with either a wet chemical, (acid, base, oxidizing treatment) or gas (halogenation) process, to physically or chemically activate the surface. Such treatments can make the tubing more easily wetted by the chemical coupling or polymer coating solutions. They can also actually introduce groups that will react with these materials, thus providing, or enhancing, chemical attachment of the hydrogel polymer to the surface.

It has been found that a strong organic base such as Choline TM, (Rohm and Haas) initially showed promise as a pretreatment procedure on silicone surfaces. Strong acids (e.g., sulfuric acid) or oxidants (e.g., calcium hypochlorite) were not as effective as the base. Then, in a series of coating trials with, and without, Choline TM base pretreatment it was determined that while aiding in initial wetting or coatability of silicone rubber, after that the base treatment was not really necessary to produce an acceptable hydrogel coated silicone tubing.

The necessity of a solvent swelling pretreatment or primer coat for silicone surfaces has been demonstrated. When Petrarch PS076 (trimethoxypropylsilyl substituted polyethyleneimine) primer is applied in this way very smooth, adherent top coats of PVP are obtained which readily convert to very slippery wet coats in water. In addition, in the prior art (1986 patent to Becton Dickinson, U.S. Pat. No. 4,589,873) a dimethyl formamide solution of PVP was claimed to be effective, when applied to solvent pre-swollen (in toluene or xylene) silicone tubing. This was shown not to work. PVP coatings simply could not be produced on silicone using this procedure. For example, xylene swollen silicone tubing was not wetted when dipped into a 4 percent PVP K-90 solution in DMF. The PVP/DMF solution drained completely away from the tubing as it was removed from the solution, leaving no liquid film on the tubing surface. (See Example XIII, Table 2).

Equilibrium swelling and percent leachables were determined for two batches of silicone tubing, as shown in Table 1. Based on this information, the primer solutions to be evaluated were prepared in either methylene chloride, a PVC solvent, or 1,1,1-trichloroethane. However, methylene chloride was determined not to be a suitable coating medium for PVC primer solutions. Alcohols such as isopropanol and methanol were determined to be much better organic media for primer application. These media do not dissolve the vinyl and thus result in much better retention of flexibility and shape.

Dipping vinyl tubing in 2-4 percent PVP/methanol solution and drying the wet tubing at 80°-150° C. in an air circulating oven for 20 minutes at 80° C. and 5 minutes at 150° C. produces a water wettable, slippery surface. A similar, qualitatively more slippery, coating is obtained using a 2-4 percent PVP solution in isopropanol and drying the same way. However these water wettable slippery coatings are easily removed by rubbing lightly with the fingers while wetted with water. After the slippery coating is gone the vinyl surface is still more readily water wetted, that is water spreads on the surface to form a film. But the slippery, lubricating property is no longer observable. On the other hand, when 0.2 percent PS076 is included in the coating solutions, the initial water wettability and slipperiness is comparable. However, the slippery property is qualitatively more durable and this effect appears to be enhanced when the coating solution is based on isopropanol rather than methanol.

EQUILIBRIUM SWELLING AND PERCENT LEACHABLES OF SILICONE TUBING IN METHYLENE CHLORIDE

| | MINUTES | | | | | | |
|---|---|---|---|---|---|---|---|
| | 30 | 60 | 90 | 120 | 150 | 210 | 270 |
| Swell, percent | | | | | | | |
| Batch # 1 (a) | 141.8 | 152.9 | 154.9 | — | — | — | — |
| Batch # 2 (b) | 165.2 | 177.8 | — | 181.5 | 190.7 | 187.4 | 188.0 |
| Weight Loss, percent | | | | | | | |
| Batch # 1 | 1.38 | 1.78 | 1.70 | — | — | — | — |
| Batch # 2 | 2.05 | — | 2.50 | — | 2.30 | — | 2.70 |
| Size change, percent: O.D. | | | | | | | |
| Batch # 1 | N.A. | N.A. | 28.9 | — | — | — | — |
| Batch # 2 | 14.3 | N.A. | 28.9 | — | — | — | 28.9 |
| Size change, percent: length | | | | | | | |
| Batch # 1 | — | — | 26.0 | — | — | — | — |
| Batch # 2 | 31.2 | — | 33.8 | — | — | — | 36.4 |

(a) First batch of silicone tubing, post cured,
(b) Second batch of silicone tubing, not post cured As a result a treatment procedure has been developed that gives a more slippery surface in water or aqueous media than untreated controls which comprises the following steps.

Application of a primer coat comprising a solution of N-trimethoxypropylsilyl polyethyleneimine (Petrarch PS076) in methylene chloride or trichloroethane on silicone and in isopropanol/methanol or isopropanol on vinyl (PVC);

Application of a tie coat comprising an aqueous solution of a pharmaceutical grade polyacrylic acid, Carbopol 940 (B.F. Goodrich), or a dimethyl formamide (DMF) solution of poly(methyl vinyl ether/maleic anhydride), Gantrez AN 169 (GAF Corp.) or a 1:1 methanol/isopropanol solution of same;

Application of a slippery coating comprising an aqueous solution of polyvinylpyrrolidone (PVP), K-90 (GAF Corp.) or an alcohol, such as n-propyl or isopropyl alcohol solution of same.

Alternatively, in treating silicone polymeric devices a pretreatment step with a quaternary organic base, for example Choline TM (Rohm & Haas) can first be carried out in order to render the silicone more susceptible to the treatment sequence outlined above.

While the invention has generally been described above, the details of the present invention will be better understood by recourse to the following examples.

EXAMPLES

General Comments

Unless otherwise indicated samples of silicone and PVC tubing were utilized throughout in demonstrating the treatment method of the present invention.

EXPERIMENTAL PROCEDURE SILICONE AND PVC TUBING

Procedure

1. Individual tubing samples were cut to 15 inches in length and then marked by cutting out notches at the end of the tubing to indicate its respective reference number. Two holes were also punched out at this same end for sample hanging during the drying step.

2. The individual tubing was immersed vertically in a 16-inch long glass tube containing the 0.2% PS076 solution (see Solutions) for 2 minutes. The tubing was then placed in an air-circulating oven at 800° C. for 15 minutes.

3. The tubing was removed from the oven, allowed to cool to room temperature for several minutes, and then dipped into an $NH_3$ treatment solution for 10 seconds. The tubing was again placed into the oven at 800° C. for a 30 minute drying time.

4. Upon removal from the oven and subsequent cooling to room temperature, the tubing was dipped into a Gantrez 169 solution for 10 seconds. Once the dipping process was complete, the tubing was again placed into the oven for 15 minutes at 800° C.

5. The final step involved slipping the tubing into the polyvinylpyrrolidone solution for 10 seconds. The same drying procedure described above was carried out, with the exception of the drying time being increased to 30 minutes.

SOLUTIONS

I. Primer Solution (N-trimethoxypropylsilyl polyethyleneimine; Petrarch PS076). The above is made up to a 0.2% solution in methylene chloride or 1,1,1-trichloroethane for silicone tubing and either methanol and/or isopropanol for the PVC tubing. The PS076 material must be kept cold and protected from moisture when not in use.

II. $NH_3$ Treatment Solution

This solution is composed of the following: 105 mls distilled water, 6 mls methanol, 0.9 mls ammonium hydroxide (29.7% $NH_3$).

III. Gantrez AN-169

Gantrez AN-169, a product of the GAF Corporation, is made up in a 0.25–5.0 percent solution in DMF or is preferably made up to a 0.25–5.0 percent solution in a 1:1 ratio of methanol and isopropanol, and more preferably a 0.25–1.0 percent solution will be used.

IV. Polyvinylpyrrolidone Solution

PVP K-90, another product of the GAF Corporation, is preferably made up to a 0.25–5.0 percent solution in distilled water. More preferably a solution of 0.25–2.0 percent will be used. The concentration level varies according to experimental needs.

EXAMPLES 1-13

A treatment procedure that gives a more slippery surface than untreated silicone controls was demonstrated in a series of treatments. The treatment steps employed were as follows:

Silicone pretreatment with a quaternary organic base (Choline, Rohm & Haas).

Primer treatment, solution of N-trimethoxypropylsilyl polyethyleneimine (Petrarch PS076) in methylene chloride.

Tie coat, aqueous solution of a pharmaceutical grade polyacrylic acid, Carbopol 940 (B.F. Goodrich) or a DMF solution of poly(methyl vinyl ether/maleic anhydride), Gantrez AN-169 (GAF Corporation).

Surface slippery coating, water solution of polyvinylpyrrolidone (PVP), K-90 (GAF Corporation).

The results of measurements taken of average force using the Porcine Skin Test is set forth in Table 2.

Tie coat, a 1:1 methanol/isopropanol solution of poly(methyl vinyl ether/maleic anhydride), Gantrez AN-169 (GAF Corporation).

Surface slippery coating, aqueous solution of polyvinylpyrrolidone (PVP), K-90 (GAF Corporation).

The results of measurements taken of average force using the Porcine Skin Test are set forth in Table 3.

A prior art procedure, taught in the patent to Becton Dickinson (U.S. Pat. No. 4,589,873) in which vinyl tubing is claimed to be coated with a DMF solution of PVP, was also repeated. It was shown that the DMF solvent quickly attacks or dissolves the surface of the vinyl tubing. The coated product is thus easily distorted and the coating produced is readily rendered very uneven and of poor quality.

Also after this wet coating is dried with a hot air gun and placed in water, the clear surface becomes wet and slippery but quickly turns white and opaque. This is an unpleasing effect aesthetically. If the coating is dried at

TABLE 2

SILICONE TUBING: TREATMENT VARIABLES

| Example No. | 18% Choline | PS076 Primber/[b] | Acid/ Base | 0.25% Carbopol | 1.5% PVP. K-90 | Porcine Skin Test Average Force Dry | Wet |
|---|---|---|---|---|---|---|---|
| 1. (control) | No treatment | — | — | — | — | 3.03 | 0.81 |
| 2. | 10 Min.[a] | X | — | X | X | 2.35 | 0.72 |
| 3. | — | X | — | X | X | 2.75 | 0.28 |
| 4. | 60 Min. | X | — | X | X | 2.88 | 0.24 |
| 5. | 30 Min. | X | — | 5% Gantrez AN169 in DMF | X | 3.20 (4.15, 2.25) | 0.3 |
| 6. | 30 Min. | X | — | X | 0.33% of Polyox WSR301 in water | 2.48 | 0.30 |
| 7. | 30 Min. | X | — | X | 0.18% of Polyox WSR CoAG in water | 2.13 | 0.94 |
| 8. | 30 Min. | X | — | X | X | 3.22 | 0.74 |
| 9. | 30 Min. | X | Acid[c] | X | — | 3.63 | 0.52 |
| 10. | 30 Min. | X | Base[d] | X | — | 3.30 | 1.73 |
| 11. (control) | No treatment | | | | | 3.03 | 0.81 |
| 12. | Flame treatment (simulated plasma), toluene solution Kraton, Selar solution | | | | | 3.30 | 0.98 |
| 13. | Swollen in Xylene 30 min., dip in 4% PVP (K-90) in DMF 5 seconds, dry | | | | | 1.33 | 0.78 |

[a]Heated with hot air gun during treatment
[b]5% (N-triemethoxsilylpropyl) polyethyleneimine (Petrarch PS076) in methylene chloride.
[c]105 ml methanol, 6 ml distilled water, 0.9 ml glacial acetic acid.
[d]105 ml methanol, 6 ml distilled water, 0.9 ml 29, 7% NH in $H_2O$ (Concentrated ammonium hydroxide).

EXAMPLES 14-28

A treatment procedure similar to the procedure utilized in Examples 1-13 has been demonstrated in a series of treatments on PVC.

The treatment steps employed were as follows:

Primer coat, solution of N-trimethoxypropylsilyl polyethyleneimine (Petrarch PS076) in isopropanol/methanol or isopropanol.

room temperature or at a relatively low temperature in an oven (e.g. 80° C. for 15 or 30 minutes), the wet coating is readily removed when rubbed between the fingers under water, while the surface becomes cloudy. If a methanol solution of PVP (4 percent) is used to coat the PVC, even when the tubing is dipped for 100 seconds, and dried at 80° C. for 30 minutes, the coating quickly dissolves and is removed with mild finger abrasion under water, yielding a non-slippery tubing.

TABLE 1

VINYL TUBING: TREATMENT VARIATION

| Example No. | 18% Choline | Primer | Acid/Base | 0.25% Carbopol | Polymer | Porcine Skin Test Average Force-(Lbs.) Dry | Wet |
|---|---|---|---|---|---|---|---|
| 14. | None | — | — | — | — | 0.73 | .51 |
| 15. | — | — | — | — | 4% of Solution of PVP (K-90) in distilled water | 1.5 | 2.4 |
| 16. | 30 min. | 5% PSO76 ($CH_2Cl_2$)[a] | — | X | 1.5% PVP(K-90)$H_2O$ | 6.90 | 2.73 |
| 17. | 30 min. | 5% PSO76 ($CH_2Cl_2$) | Base[b] | X | — | 3.40 | 1.60 |
| 18. | — | — | — | — | 1.5%(NMP)pvp/selar | 0.98 | 0.33 |
| 19. | — | — | — | — | 1.5% Elvamide 8061/PVP (MeOH) | 1.73 | 1.15 |
| 20. | — | 0.34% polyethylene imine (PEI)[c] | — | — | 1.5% Elvamide 8061/PVP (MeOH) | 1.36 | 0.76 |

TABLE 1-continued
VINYL TUBING: TREATMENT VARIATION

| Example No. | 18% Choline | Primer | 0.25% Acid/Base | Carbopol | Polymer | Porcine Skin Test Average Force-(Lbs.) Dry | Wet |
|---|---|---|---|---|---|---|---|
| 21. | — | — | — | — | 1.5% Elvamide 8061/PVP (MeOH) | 1.39 | 1.01 |
| 22. | — | — | — | — | 1.5% Elvamide 8061/PEO-500 (MeOH) | 1.38 | 1.03 |
| 23. | — | — | — | — | 1.5% Elvamide 8061/Klucal LF (MeOH/IPA) | 1.31 | 0.38 |
| 24. | — | — | — | — | 1.5% Elvamide 8061/Klucal HF (MeOH/IPA) | 1.60 | 1.40 |
| 25. | — | 0.34% PEI | — | — | 1.5% Elvamide 8061/PVP (MeO/IPA) | 1.35 | 0.30 |
| 26. | — | 0.34% PEI | — | — | 1.5% Elvamide 8061/PEC −500 (MeOH/IPA) | 1.25 | 0.63 |
| 27. | — | 0.34% PEI | — | — | 1.5% Elvamide 8061 Klucal LF (MeOH/IPA) | 1.15 | 0.33 |
| 28. | — | 0.34% PEI | — | — | 1.5% Elvamide 8061/Klucal LF (MeOH/IPA) | 1.26 | 0.61 |

(a) 5% (N-trimethoxsilylpropyl)polyethyleimine (Petrarch PS076) in methylene chloride
(b) $NH_3$ treatment/1: 0.9 ml of $NH_3OH$ (29.7% $NH_3$). 105 ml water, 6 ml methanol.
(c) 0.34% polyethyleneimine prepared from 33% aqueous solution (PEI600, Cordova Chemical) diluted with methanol An evaluation of the various coating components was made for both silicone and PVC coatings tested. The results are shown in Tables 4–6. The best components found were as follows:

Primer, PS076 in trichloroethane for silicone; in isopropanol/methanol or isopropanol alone for PVC.

Tie coat, Gantrez AN 169 in 1:1 methanol/isopropanol.

Surface slippery coating, PVP K-90 in water.

TABLE 4
PRIMERS EVALUATED

| Tubing | Type | Comment |
|---|---|---|
| Silicon | Silane coupling agents | PSO76 the "polymeric" coupling agent is best of series |
| | Ganex V-220 -olefin/vinyl pyrrolidone copolymer | Treatment looked promising. Same pendant group as on PVP |
| | Gantrez AN-169 in MeOH/IPA, pendant half esters of maleic anhydride | Treatment looked promising |
| | Kraton, Styrene/isoprene/styrene block copolymer | Works on flame treated silicone simulated plasma treatment |
| PVC | Silane coupling agent Polyethyleneimine | PS076 works well Not as slippery as control |

TABLE 5
TIE COATS EVALUATED

| Type | Comment |
|---|---|
| Carbopol, based on polyacrylic acid | Second best |
| Gantrez AN-169, pendant maleic anhydride (a) | Slippery |
| Gantrez AN-169 methyl half ester in MeOH/IPA | Best |
| Gantrez ES, preformed half esters of maleic anhydride | Ethyl half ester, Gantrez ES 225 best of series but noticeably less slippery than Gantrez AN-169 methyl half ester in IPA/MeOH (50:50) |
| Michem Prime 4983, ethylene acrylic acid Dispersed in aqueous $NH_3$ | Results in appreciably less wettable and slippery PVP top coats |

(a) Hydrolyzes to maleic acid during PVP top coat application.

TABLE 6
POLYMERS EVALUATED

| Type | Comments |
|---|---|
| PVP, polyvinylpyrrolidone | Best |
| Selar, ethylene vinyl alcohol copolymer | Adds strengths, decreases slipperiness when combined with PVP |
| Gantrez AN-169, pendant maleic anhydride | Tested combination with PVP/Selar |
| Elvamide 8061, nylon | Combined with Klucel gave slippery coating |
| Klucel, Hydroxypropyl cellulose | Combined with Elvamide 8061 gave slippery coating |
| PEOX, poly (ethyl oxazoline) | Combined with Elvamide 8061 gave slippery coating with poor strength |
| Polyox, polyethylene oxide | No improvement seen |
| Kynar 461, polyvinylidene fluoride | With no primer, coated nearly same as control; (silicone) |

EXAMPLE 29–60

Using the procedures previously employed in Examples 1–28 a series of further evaluations of various components were carried out using the materials set out in Tables 7–9.

The results of evaluations performed are also set out in Tables 7–9.

TABLE 7

TREATMENTS GIVING EVEN SLIPPERY DURABLE COATINGS ON SILICONE RUBBER (a)

| Example Number | Conc. Choline Percent | Primer (b) | Post-Primer (c) | Tie Coat | 1.5% PVP, $H_2O$ | Bovine Skin Test Average Force, Lbs. Dry | Wet | % Reduction in force (e) |
|---|---|---|---|---|---|---|---|---|
| 1 | — | — | — | — | — | 3.03 | 0.81 (d) | — |
| 3 | — | 5% PSO76 ($CH_2Cl_2$) | — | 0.25% Carbopol ($H_2O$) | + | 2.75 | 0.28 | 65 |
| 29 | 2.25% | 5% PSO76 ($CH_2Cl_2$) | #1 | 0.25% Carbopol ($H_2O$) | + | 1.44 | 0.38 | 53 |
| 30 | | | | | | — | 0.47 (d) | |
| 31 | 15% | — | — | 0.25% Carbopol ($H_2O$) | + | 1.68 | 0.38 | 19 |
| 32 | | | | | | 1.40 | 0.23 | 51 |
| 33 | — | 2% PSO76 ($CH_2Cl_2$) | #3 | 0.5% Gantrez AN169 in MeOH/IPA | + | 1.39 | 0.34 | 15 |
| 34 | — | 3% PSO76 ($CH_2Cl_2$) | #3 | 0.5% Gantrez AN169 in MeOH/IPA | + | 1.89 | 0.27 | 43 |
| 35 | — | 1% Ganex V-220 (TCE) | — | 0.25% Carbopol ($H_2O$) | + | 1.0 | 0.27 | 43 |
| 36 | 15% | — | — | 0.5% Gantrez AN169 in MeOH/IPA | + | 1.45 | 0.22 | 53 |

(a) Coated tubing pulled through a hole bored in fresh bovine skin, dry and wetted with water at room, temperature.
(b) $CH_2Cl_2$ = methylene chloride: TCE = trichloroethane.
(c) Ammonia treatment number 1: A solution of 0.9 ml $NH_4OH$ (29.7% $NH_3$). 105 ml methanol, 6 ml water, treatment number.
(d) Variation in wetted control value: 0.81 for examples 3 and 29; 0.47 for Examples 32–36.
(e) Percent reduction in force = $\dfrac{\text{Force Control} - \text{Force Sample}}{\text{Force Control}} \times 100$

TABLE 8

TREATMENTS GIVING EVEN SLIPPERY DURABLE COATINGS ON SILICONE RUBBER (a)

| Example Number | Conc. Choline, Percent | Primer (b) | Post-Primer (c) | Tie Coat | 1.5% PVP, $H_2O$ | Silicone Slip, (a) Test Average Force, Pounds | % Reduction in force (e) |
|---|---|---|---|---|---|---|---|
| 37 | — | — | — | — | — | 0.41 | |
| 33 | — | 2% PSO76 ($CH_2Cl_2$) | #3 | 0.5% Gantrez (MeOH/IPA) | + | 0.39 | 5 |
| 34 | — | 3% PSO76 ($CH_2Cl_2$) | #3 | 0.5% Gantrez (MeOH/IPA) | + | 0.39 | 5 |
| 36 | 15 | — | — | 0.5% Gantrez (MeOH/IPA) | + | 0.35 | 15 |
| 37 | — | — | — | — | — | 0.31 | |
| 38 | — | 1% PSO76 ($CH_2Cl_2$) | #3 | 0.5% Gantrez AN169 | + | 0.06–0.10 | 68–81 |
| 39 | — | 1% PSO76 ($CH_2Cl_2$) | #3 | " | + | 0.13–0.21 | 32–58 |
| 40 | — | 1% PSO76 ($CH_2Cl_2$) | #3 | " | + | 0.03–0.09 | 71–90 |
| 41 | — | 0.5% PSO76 | — | 0.5% Gantrez AN169 | + | 0.06–0.12 | 61–81 |
| 42 | — | 0.5% PSO76 (TCE) | #3 | " | + | 0.17–0.22 | 29–45 |

(a) Coated tubing pulled, water wetted, through a punched hole in a silicone rubber sheet
(b) $CH_2Cl_2$ = methylene chloride; TCE = trichloroethane.
(c) Ammonia treatment number 3: A solution of 0.9 ml $NH_4OH$ (29.7% $NH_3$), 6 ml methanol, and 106 ml water
(d) Variation in wetted control value: 0.41 for example 37 and 0.31 for examples 38–42.
(e) Percent reduction in force = $\dfrac{\text{Force Control} - \text{Force Sample}}{\text{Force Control}} \times 100$

TABLE 9

QUALITATIVE RANKING OF PVC TUBING TREATMENTS (a)

| Ranking | Example Number | Primer (b) | $NH_3$ (c) Treatment Number | Tie Coat | PVP (K-90) in $H_2O$ | % Reduction (d) Force From Silicone Slip Test (a) |
|---|---|---|---|---|---|---|
| 1 | 43 | 0.1% PSO76 (MeOH/IPA) | 3 | 0.5% Gantrez AN169 (1:1 MeOH/IPA) | 1.5% | 81 |
| | 44 | 0.1% PSO76 (MeOH/IPA) | — | 0.5% Gantrez AN169 (1:1 MeOH/IPA) | " | 75–81 |
| | 45 | 0.2% PSO76 | 3 | 0.5% Gantrez AN169 (1:1 MeOH/IPA) | " | 81 |
| | 46 | " | — | 0.5% Gantrez AN169 (1:1 MeOH/IPA) | " | 78–84 |
| 2 | 47 | 0.2% PSO76 (MeOH/IPA) | 3 | 0.25% Gantrez AN169 (1:1 MeOH/IPA) | 0.75% | 75 |
| 3 | 48 | 0.2% PSO76 (Me)H/IPA) | 3 | 0.25% Gantrez AN169 (1:1 MeOH/IPA) | 0.75% | 76 |
| | 49 | 0.2% PSO76 | 3 | 1.0% Gantrez AN169 (1:1 MeOH/IPA) | 3.0% | 73 |

TABLE 9-continued

QUALITATIVE RANKING OF PVC TUBING TREATMENTS (a)

| Ranking | Example Number | Primer (b) | NH₃ (c) Treatment Number | Tie Coat | PVP (K-90) in H₂O | % Reduction (d) Force From Silicone Slip Test (a) |
|---|---|---|---|---|---|---|
| 4 | 50 | 0.2% PSO76 (MeOH/IPA) | 3 | 0.5% Gantrez AN169 in methanol + ammonia combined with 3.0% PVP | 5% | 75 |
| 5 | 51 | 0.2% PSO76 (IPA) | 3 | 0.5% Gantrez AN169 (1:1 MeOH/IPA) | 1.5% | 73 |

(a) Coated tubing pulled, water wetted, through a slit in a silicone rubber sheet.
(b) IPA = isopropanol, MeOH = Methanol.
(c) Ammonia treatment number 3: A solution of 0.9 ml NH₄OH (29.7% NH₃), 6 ml methanol, and 106 ml water.
(d) Percent reduction in force = $\frac{\text{Force Control} - \text{Force Sample}}{\text{Force Control}} \times 100$

TABLE 10

QUALITATIVE RANKING OF SILICONE TUBING TREATMENTS (a)

| Ranking | Example Number | Primer (b) | NH₃ (c) Treatment Number | Tie Coat | PVP (K-90) in H₂O | % Reduction (d) Force From Silicone Slip Test (a) |
|---|---|---|---|---|---|---|
| 1 | 52 | 0.2% PSO76(CH₂Cl₂) | 3 | 0.25% Gantrez AN169 (1:1 MeOH/IPA) | 0.75% | 75% |
| 2 | 53 | 0.5% PSO76 | 3 | 0.5% Gantrez AN169 (1:1 MeOH/IPA) | 1.5% | 33 (d) |
| 3 | 54 | 0.5% PSO76(TCE) | 3 | 0.5% Gantrez AN169 (1:1 MeOH/IPA) | 1.5% | 61–81 |
| 4 | 55 | 0.2% PSO76(TCE) | 3 | 0.25% Gantrez AN169 (1:1 MeOH/IPA) | 1.5% | 73 |
| 5 | 56 | 0.2% PSO76(TCE) | 3 | 0.5% Gantrez AN169 (1:1 MeOH/IPA) | 1.5% | 73 (e) |
| 6 | 57 | 0.5% PS404(TCE) | 3 | 0.5% Gatnrez AN169 (1:1MeOH/IPA) | 1.5% | 29 |
|  | 58 | 1.0% PS404(TCE) | 3 | 0.5% Gatnrez AN169 (1:1MeOH/IPA) | 1.5% | 58 |
| 7 | 59 | 0.5% PSO78.5(TCE) | 3 | 0.5% Gantrez AN169 | 1.5% | 54 |
|  | 60 | 1.0% PSO78.5(TCE) | 3 | " | 1.5% | 50 |

(a) Coated tubing pulled, water wetted, through a slit in a silicone rubber sheet.
(b) CH₂CL₂ = methylene chloride; TCE = trichloroethane; PS 404 = Petrarch T-Structure Polydimethylsiloxane with Epoxy cyclohexylethyl functionality at branch points; PSO78.5 = Petrarch Triethoxysilyl Modified Polybutadiene.
(c) Ammonia treatment number 3: A solution of 0.9 ml NH₄OH (29.7% NH₃), 6 ml methanol, and 106 ml water.
(d) Percent reduction in force = $\frac{\text{Force Control} - \text{Force Sample}}{\text{Force Control}} \times 100$
(e) Based on porcine wetted skin test result.
(f) Result for nonpostcured tubing.

While the invention has been described with respect to various specific examples and embodiments it is to be understood that the invention is not limited thereto and that it can be variously practiced within the scope of the following claims.

We claim:

1. A process for treating a medical article or device having a polymeric surface to produce a smooth, durable, slippery coating comprising:
   applying to the polymeric surface of the said article or device a primer coat;
   applying to said surface a tie coat comprising a solution selected from aqueous solutions of polyacrylic acid, dimethyl formamide solutions of poly(methyl vinyl ether/maleic anhydride), 1:1 methanol/isopropanol solutions of poly(methyl vinyl ether/maleic anhydride) and solutions of poly(methyl vinyl ether/maleic anhydride) in one or more alcohols selected from the group comprising the lower alcohols of methanol through pentanol or mixtures thereof in water; and
   applying to said surface a slippery coating comprising a solution of polyvinylpyrrolidone.

2. The process of claim 1 wherein the article has a polymeric surface selected from the group comprising silicone, polyvinyl chloride, latex, polyester, polyurethane and thermoplastic elastomers.

3. The process of claim 2 wherein the surface of the article or device is first pretreated with a quaternary organic base prior to applying the tie coat.

4. The process of claim 2 wherein the primer coat applied comprises a solution of N-trimethoxypropylsilyl polyethyleneimine in methylene chloride 5. The process of claim 2 wherein the tie coat applied comprises a solution selected from aqueous solutions of polyacrylic acids, dimethyl formamide solutions of poly(methyl vinyl ether/maleic anhydride), and 1:1 methanol/isopropanol solutions of poly(methyl vinyl ether/maleic anhydride).

6. The process of claim 2 wherein the primer coat applied comprises a solution of N-trimethoxypropylsilyl polyethyleneimine in isopropanol or in an isopropanol/methanol mixture.

7. The process of claim 2 wherein the tie coat applied comprises a 1:1 methanol/isopropanol solution of poly(methyl vinyl ether/maleic anhydride).

8. The process of claim 1 wherein the polymeric surface is silicone, latex, polyester, polyurethane and thermoplastic, the primer coat to be applied is a solution of N-trimethoxypropylsilyl polyethyleneimine in trichloroethane, the tie coat to be applied is a solution of poly(methyl vinyl ether/maleic anhydride) in 1:1 methanol/isopropanol, and the slippery coating to be applied is a solution of polyvinylpyrrolidone in water.

9. A medical article or device having a polymeric surface which has been treated to produce a smooth, durable, slippery coating, said coating being formed by applying to the polymeric surface of the said article or device a primer coat comprising a solution selected from aqueous solutions of polyacrylic acid, dimethyl formamide solutions of poly(methyl vinyl ether/maleic anhydride) and 1:1 methanol/isopropanol solutions of poly(methyl vinyl ether/maleic anhydride); and applying to said surface a slippery coating comprising a solution of polyvinylpyrrolidone.

10. An article or device having a silicone, latex, polyester, polyurethane and thermoplastic surface treated in accordance with claims 5 and 6.

11. An article or device having a polymeric surface treated in accordance with claim 8.

12. An article or device having a polymeric surface treated in accordance with claim 1 which is tubular in shape.

13. An article or device having a polymeric surface treated in accordance with claim 1 which is flat in shape.

14. An article or device having a polymeric surface treated in accordance with claim 1 which is suitable for use in surgical procedures.

15. An article or device having a polymeric surface treated in accordance with claim 1 which is suitable for use as a drainage device.

16. An article or device having a polymeric surface treated in accordance with claim 1 which treated surface is suitable to withstand the rigors of sterilization by steam.

* * * * *